(12) United States Patent
Butte et al.

(10) Patent No.: US 8,750,652 B2
(45) Date of Patent: Jun. 10, 2014

(54) MICROFLUIDIC WAVEGUIDE DETECTOR

(75) Inventors: Manish J. Butte, Stanford, CA (US);
John J. LeBlanc, North Andover, MA (US)

(73) Assignees: The Board of Trustees of the Leland Stanford Junior University, Palo Alto, CA (US); The Charles Stark Draper Laboratory, Inc., Cambridge, MA (US)

( * ) Notice: Subject to any disclaimer, the term of this patent is extended or adjusted under 35 U.S.C. 154(b) by 345 days.

(21) Appl. No.: 13/317,180

(22) Filed: Oct. 12, 2011

(65) Prior Publication Data
US 2012/0087618 A1    Apr. 12, 2012

Related U.S. Application Data

(60) Provisional application No. 61/404,926, filed on Oct. 12, 2010.

(51) Int. Cl.
*G02B 6/26* (2006.01)
(52) U.S. Cl.
USPC .............................................. 385/12; 385/30
(58) Field of Classification Search
None
See application file for complete search history.

(56) References Cited

U.S. PATENT DOCUMENTS

| | | | | |
|---|---|---|---|---|
| 4,857,273 | A * | 8/1989 | Stewart | 422/82.11 |
| 5,344,784 | A * | 9/1994 | Attridge | 436/518 |
| 6,198,869 | B1 * | 3/2001 | Kraus et al. | 385/129 |
| 7,175,811 | B2 * | 2/2007 | Bach et al. | 422/82.11 |
| 7,385,460 | B1 * | 6/2008 | Wang et al. | 333/108 |
| 7,391,936 | B2 | 6/2008 | Pau et al. | |
| 2002/0005354 | A1 * | 1/2002 | Spence et al. | 204/450 |
| 2002/0031836 | A1 * | 3/2002 | Feldstein | 436/180 |
| 2004/0091397 | A1 * | 5/2004 | Picard | 422/99 |
| 2006/0147147 | A1 * | 7/2006 | Zourob et al. | 385/12 |
| 2007/0197888 | A1 * | 8/2007 | Axelrod et al. | 600/339 |
| 2009/0296083 | A1 * | 12/2009 | Saaski et al. | 356/246 |
| 2010/0065726 | A1 | 3/2010 | Zhong et al. | |
| 2013/0157283 | A1 * | 6/2013 | Yung et al. | 435/7.1 |

FOREIGN PATENT DOCUMENTS

JP    8-29330 A  *  2/1996

* cited by examiner

*Primary Examiner* — Mike Stahl
(74) *Attorney, Agent, or Firm* — Lumen Patent Firm

(57) ABSTRACT

A microfluidic detection device is provided that includes a planar waveguide, or an ion-exchange planar waveguide, a microfluidic channel disposed on the planar waveguide, a light source, such as a laser, LED or incandescent light, directed through the planar waveguide, a labeled cell disposed in the microfluidic channel, where the labeled cell lies in an evanescent field extending from the planar waveguide, and a light detector disposed to receive light from the light source through the planar waveguide. The evanescent field interacts with the labeled cell, where the light through the planar waveguide is altered according to a presence of the labeled cell in the microfluidic channel.

7 Claims, 6 Drawing Sheets

MICROFLUIDIC WAVEGUIDE DETECTOR

CROSS-REFERENCE TO RELATED APPLICATIONS

This application claims priority from U.S. Provisional Patent Application 61/404,926 filed Oct. 12, 2010, which is incorporated herein by reference.

FEDERALLY-SPONSORED RESEARCH OR DEVELOPMENT

This invention was made with Government support under contracts RR025742 and RR025744 awarded by the National Institutes of Health. The Government has certain rights in this invention.

FIELD OF THE INVENTION

The invention relates to blood cell analysis devices. More particularly, the invention relates to a low-cost optical blood cell counting waveguide device.

BACKGROUND OF THE INVENTION

Detection devices for analyzing blood cell counts have been found to be expensive due to their complexity and generally large scale. What is needed is a device and method of counting blood cells that is low cost and relatively simple to implement while providing useful detection sensitivities.

SUMMARY OF THE INVENTION

To address the shortcomings in the art, a microfluidic detection device is provided that includes a planar waveguide, a microfluidic channel disposed on the planar waveguide, a light source directed through the planar waveguide, a labeled cell disposed in the microfluidic channel, where the labeled cell lies in an evanescent field extending from the planar waveguide, and a light detector disposed to receive light from the light source through the planar waveguide, where the evanescent field interacts with the labeled cell, where the light through the planar waveguide is altered according to a presence of the labeled cell in the microfluidic channel.

In one aspect of the invention, the planar waveguide includes an ion-exchange planar waveguide.

In a further aspect of the invention, the planar waveguide has a first layer disposed deposited between a pair of second layers, where the first layer has a first refractive index and the second layers have a second refractive index, where the first refractive index is higher than the second refractive index, where light can be transported through the first layer. Here, the planar waveguide the first layer can be glass, where the second layers can be SU-8 photoresist.

In another aspect of the invention, the microfluidic channel includes a sample input, a sample output, a reagent input, a detection zone, and a reagent output.

According to a further aspect of the invention, the labeled cell can include gold, iron, silver, tin, lead, magnesium, aluminum, selenium, platinum, mercury, erbium, terbium, nickel, cadmium, uranium, and composites salts or alloys thereof.

In one aspect of the invention, the ion-exchange waveguide is made from material that includes potassium or silver salts.

In yet another aspect of the invention, the light source can be a laser, LED or incandescent light.

DETAILED DESCRIPTION

A microfluidic device is provided that allows low-cost and rapid quantitation of cells. In one embodiment, the device uses immobilized antibodies and adhesion molecules in a microfluidic channel to capture cells from a drop of blood or other sample under test. The captured cells can be labeled with gold nanoparticles, for example, using an antibody that is specific for the cell type, and metallic silver, for example, can be catalytically precipitated onto the cells. A planar waveguide lies beneath the microfluidic channel such that the evanescent field of the waveguide extends into the lumen of the microfluidic channel. Light is sent into the waveguide (such as a laser, LED or incandescent light) and emits out the other end of the waveguide. Metal-labeled cells lying in the evanescent field, in the microfluidic channel space, diminish the energy transmitted through the waveguide by interacting with the evanescent field. A photodetector is disposed to measure the intensity of light leaving the waveguide to provide a quantitation of the cells lying in the microfluidic channel. The approach lends itself to easy, parallel multiplexing such that the same drop of blood or sample can be interrogated for many cell types.

According to the invention the label material of the cell can include gold, iron, silver, tin, lead, magnesium, aluminum, selenium, platinum, mercury, erbium, terbium, nickel, cadmium, uranium, and composites salts or alloys thereof.

Figure 1:
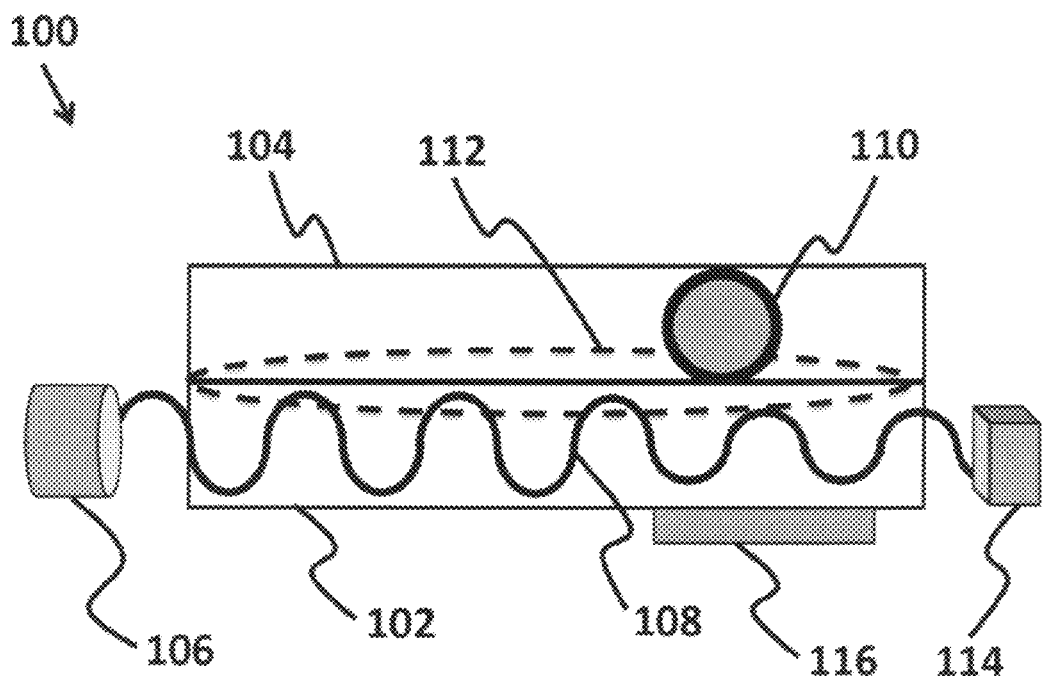
FIG. 1 shows a schematic view of a microfluidic detection device, according to one embodiment of the invention.

FIG. 1 shows a schematic planar view of a microfluidic detection device 100, according to one embodiment of the invention. A planar waveguide 102 is provided, a microfluidic channel 104 disposed on the planar waveguide, a light source 106 directs light 108 through the planar waveguide 102, a labeled cell 110 disposed in the microfluidic channel 104, where the labeled cell 110 lies in an evanescent field 112 extending from the planar waveguide 102, and a light detector 114 disposed to receive light 108 from the light source 106 through the planar waveguide 102. According to the invention, the evanescent field 112 interacts with the labeled cell 110, and the light 108 through the planar waveguide 102 is altered according to a presence of the labeled cell 110 in the microfluidic channel 104. In one embodiment, a magnet 116 is beneath the waveguide 102 to facilitate capture of ferromagnetically-tagged cells within the channel 104.

In one example, the evanescent field is used to interact with captured cells in a sample, for example T cells or B cells in blood. According to the invention, the evanescent field 112 is attenuated proportionally to the number of captured cells, that is, labeled cells 110 in the channel 104 serve as efficient loss points along the guide.

Figure 2:
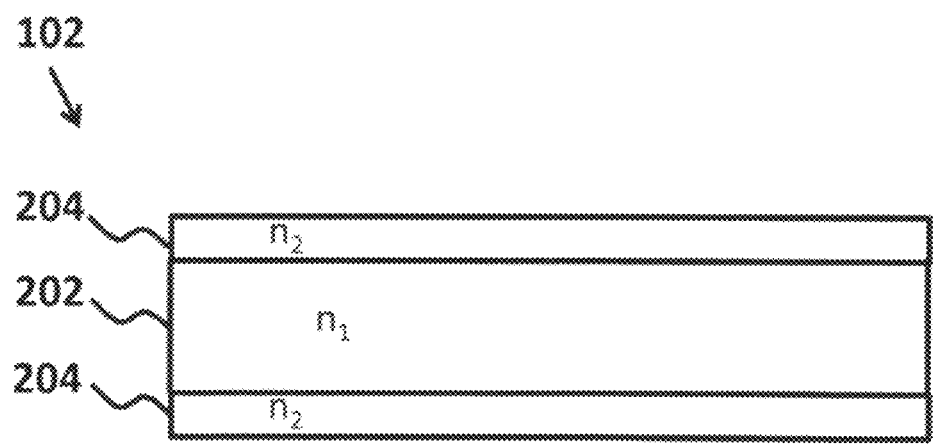
FIG. 2 shows a schematic view of a planar waveguide.

For optical waveguiding to occur, a high index core must be surrounded by a low index "cladding" material. FIG. 2 shows a planar waveguide 102 having a first layer 202 disposed between a pair of second layers 204, where the first layer has a first refractive index $n_1$ and the second layers have a second refractive index $n_2$, where the first refractive index is higher than the second refractive index, where light can be transported trough the first layer 202. Here, the planar waveguide first layer 202 can be glass, where, according to one embodiment of the invention, the second layers 204 can be SU-8 photoresist.

According to one embodiment, the planar waveguide 102 can be an ion-exchange planar waveguide. An ion-exchange process is provided, according to one embodiment of the invention, where glass is immersed in a molten alkali salt bath, allowing ions from the bath to exchange with mobile ions in the glass. The glass ion, such as Na+, has a high mobility and can be found in soda lime and borosilicate glasses. Because the waveguides 102 are diffused into the surface of a glass wafer, a flat substrate remains. This makes them an ideal to build microfluidic devices 100. The index changes achievable with ion-exchanged waveguides make them relatively easy to integrate with fibers. In one embodiment, a K+-Na+ ion exchange system is used, where this is known to produce low loss waveguides with an index change $\Delta n$ comparable to optical fibers. This is advantageous for coupling fibers to the waveguide.

One example of the ion-exchange waveguide fabrication process includes using Schott BK7 glass wafers that were cleaned with piranha solution (3:1 mixture of concentrated sulfuric acid and 30% hydrogen peroxide). A 500 nm thick aluminum film was deposited on the wafers by magnetron sputtering. The glass wafers were then covered with Shipley 1822 photoresist by spin coating at 3000 rpm with HMDS spun on as an adhesion promoter prior to the application of the photoresist. After soft baking (100° C. for 30 min), the wafers were exposed to UV in a mask aligner using a chrome mask to define a linear patterns, where the waveguides will lie. After post-exposure baking and developing, the exposed aluminum is etched using Transcene Type A Aluminum Etchant (50° C. until visual stop). Residual photoresist was removed with acetone and oxygen plasma. The glass wafers with the aluminum masking layer were submerged in a molten salt bath composed of 0.75 wt % $KNO_3$+99.25 wt % $NaNO_3$ at 350° C. for 1 hour. The glass was then cleaned and stripped of the aluminum film. The waveguides were diced using a diamond saw (Disco DAD321), then the waveguide ends were polished with diamond paper of sequentially smaller size grit, on an Allied Multi-Prep polishing tool, ending with a 0.5 μm diamond grit.

Figure 3A:
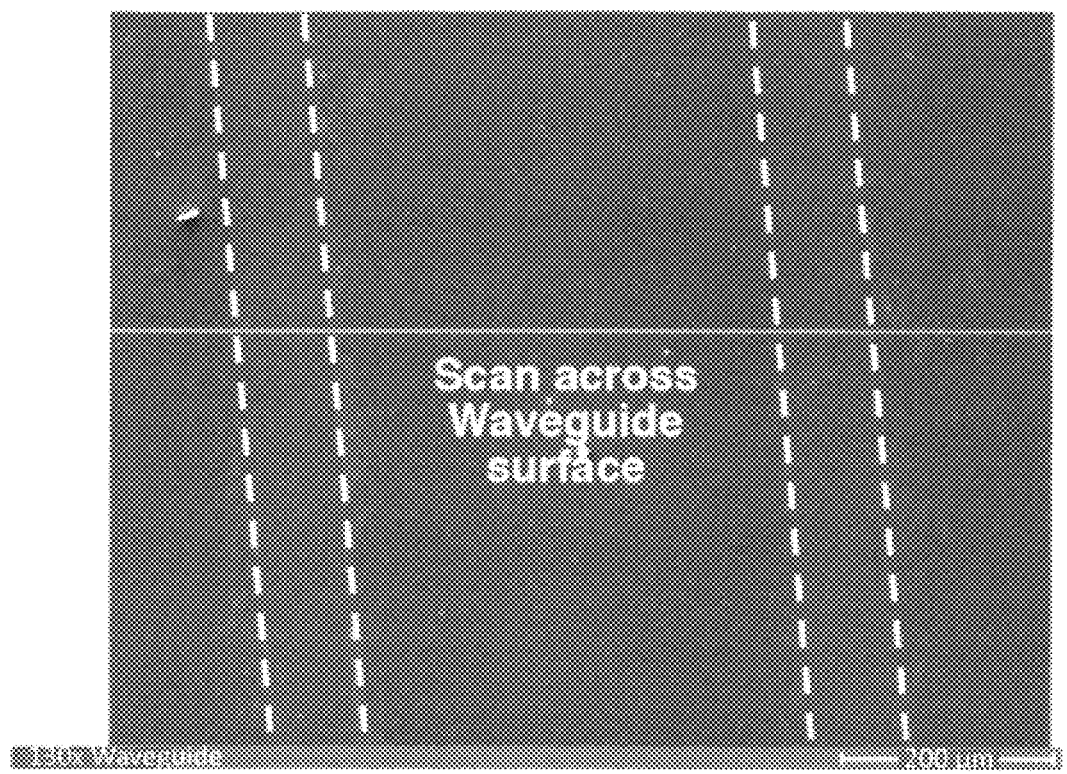
FIGS. 3a-3b show elemental analysis of potassium enrichment into the ion-exchange waveguide, according to one embodiment of the invention.
Figure 3B:
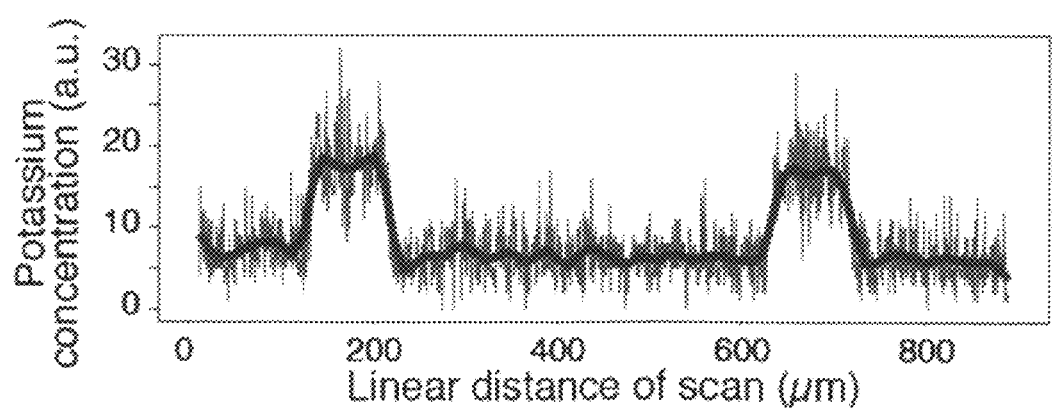

To analyze the doped layer of potassium, an Energy-Dispersive Xray spectroscopy (EDX) was used on the surface and on a cut edge of the glass. It was seen that potassium was enhanced in the ion-exchange waveguide regions by 2.4 fold when scanning across the surface (FIG. 3*a*), and similarly at the cut edge, as compared to bulk glass (FIG. 3*b*). Elemental analysis also showed that potassium was enriched to a depth of ~6.5 μm, as compared to bulk glass. The potassium signal was noted to begin at ~350 nm depth, confirming that the enriched potassium was buried at a shallow depth. In FIG. 3*a*, elemental analysis of potassium concentration was provided across the surface of the glass (solid scan line), which shows enrichment in the waveguide stripes (highlighted with white dashed lines). FIG. 3*b* shows a gray, raw data line of the measured the potassium concentration in arbitrary units. The solid line is a smoothed fit of gray raw data line. This elemental analysis shows that potassium was enriched comparing the shallow buried waveguide and bulk glass. Using a scanning electron microscope along a cut edge from the surface into the bulk glass, potassium enrichment extended ~6.5 μm and was noted to be buried at a shallow depth (~300 nm) as compared with the surface. In one aspect of the invention, the ion-exchange waveguide can be made from material that includes potassium or silver salts.

This invention is useful for various medical applications such as counting cells in blood. Other uses include:
1) Count T cells from newborn blood to diagnose Severe Combined Immune Deficiency (SCID).
2) Count B cells from newborn blood to diagnose congenital agammaglobulinemias.
3) Count neutrophils from newborn blood to diagnose congenital neutropenias.
4) Count neutrophils and immature neutrophils from the blood to diagnose sepsis or other serious bacterial, viral, fungal, or parasitic infections early.
5) Count eosinophils and neutrophils and lymphocytes from nasal secretions to diagnose allergic rhinitis versus upper respiratory viral infections versus sinus infections.
6) Count neutrophils from the blood to diagnose readiness for cycles of chemotherapy (e.g., in cycles of breast cancer therapy)
7) Count B cells from blood to diagnose readiness for cycles of anti-B cell therapy (e.g., lymphoma or autoimmune disease).
8) Count platelets from blood to diagnose the potential for bleeding disorders.
9) Count naive T cells in the blood to reveal immune reconstitution following bone marrow transplant.
10) Count CD4 T cells in the blood to diagnose HIV/AIDS or to diagnose the need for prophylactic antibiotics or change in HAART regimen in HIV/AIDS.
11) Count tumor cells from the blood, urine, CSF, or other biofluids to detect the metastasis or recurrence of cancer.

Figure 4:
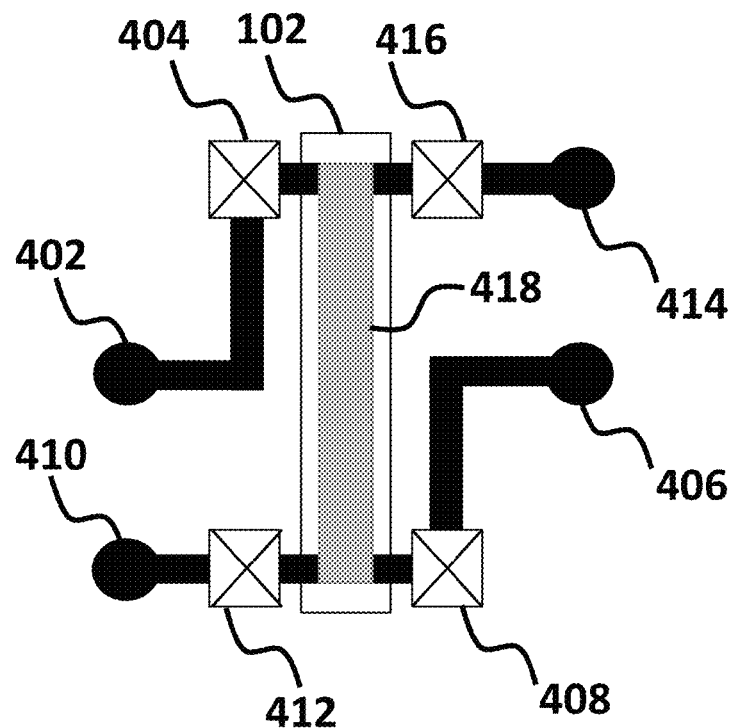
FIG. 4 shows a schematic view of the microfluidic channel, according to one embodiment of the invention.

FIG. 4 shows a schematic view of the microfluidic channels 104 disposed on the waveguide 102, according to one embodiment of the invention. In one embodiment, the microfluidic channels 104 were prepared using soft lithography. A transparency mask was laser photo-plotted with channels 100 μm wide. SU-8 photoresist was spun onto a Si wafer 25 μm thick, patterned by ultraviolet light shining through the mask, developed, then used as a relief mold for casting poly-dimethylsiloxane (PDMS), which was then sealed to glass. As shown in FIG. 4, the channels have a sample inlet 402 and sample inlet valve 404, a sample outlet 406 sample outlet valve 408, for example for processing blood. Further shown are a reagent inlet 410 and a reagent inlet valve 412 plus and a reagent outlet 414 and a reagent outlet valve 416. The reagents and samples are input and output from a detection zone 418.

According to one embodiment, the channels are prepared by injecting a hydrophilic silane, then antibodies specific for the cells to be captured (e.g., anti-CD3ε for T cells). The entire volume of the channels is as much as 10 μL, which enables very low reagent costs and very little sample requirement (i.e., less than one drop of blood).

Figure 5A:
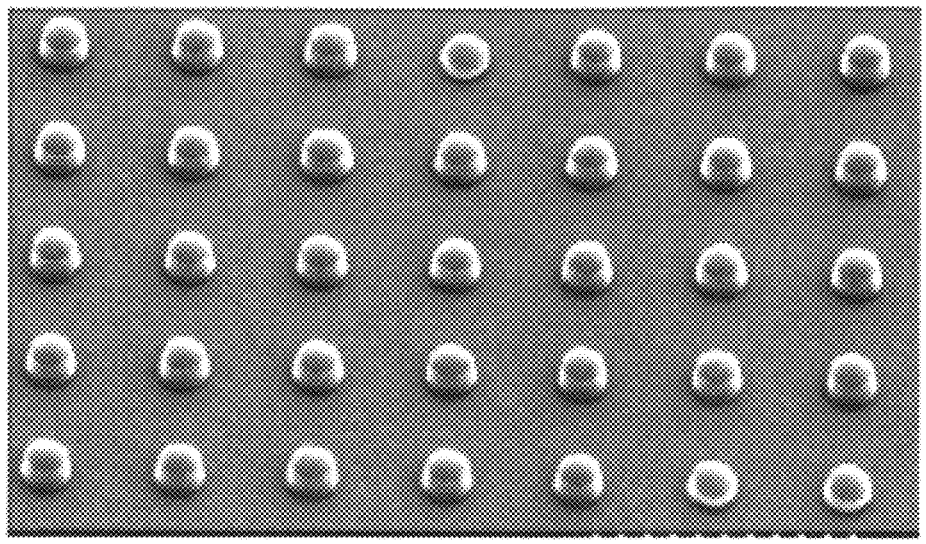
FIGS. 5a-5b show scanning electron microscope images of labeled faux T cells, according to one embodiment of the invention.
Figure 5B:
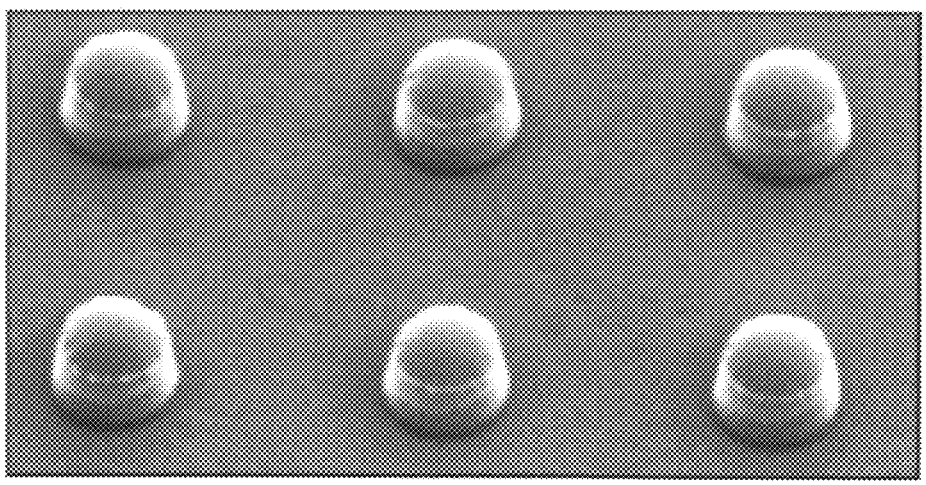
Figure 6:
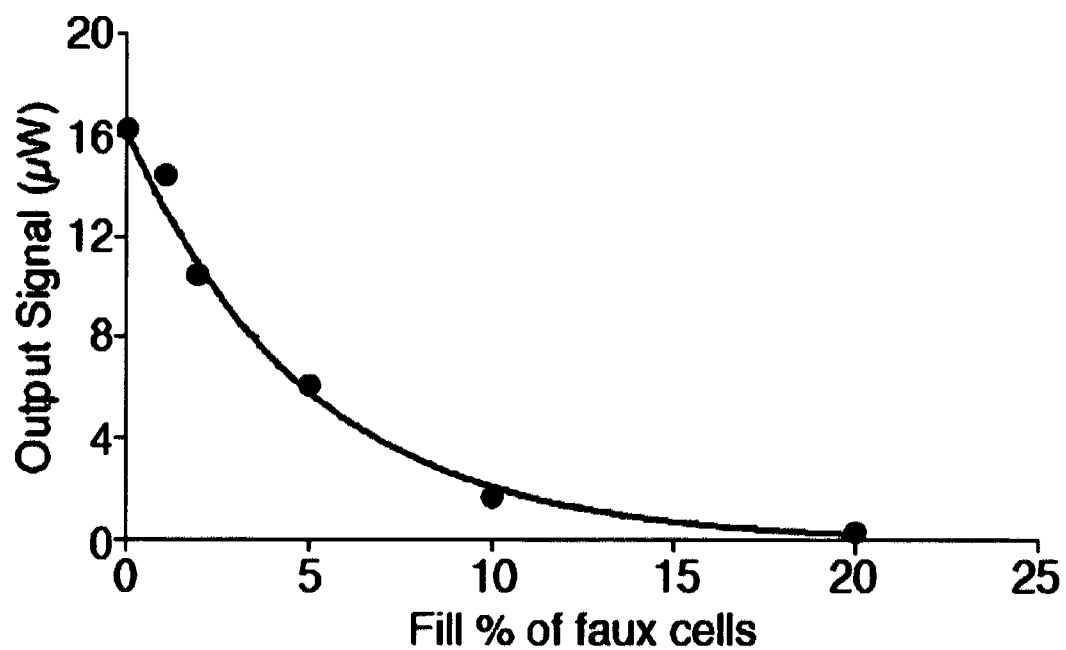
FIG. 6 shows a graph of the output signal from the waveguide versus the number of the number of faux cells, according to one embodiment of the invention.

To demonstrate the waveguides efficacy in quantitatively measuring the faux cells, cell-sized metal-coated objects were prepared out of reflowed photoresist (FIGS. 5*a*-5*b*). These objects were designed to be sized approximately as a typical lymphocyte from human blood (~5 μm) and were called "faux cells". To test a broad range of faux cells, a pattern of coverage was developed, where 0%, 1%, 2%, 5%, 10% or 20% of the surface area of the waveguide is covered by faux T cells (FIG. 5a). AZ1518 was chosen because of its ability to reflow into cell-shaped objects, and its suitable material properties. AZ1518 was patterned on the waveguides as faux cells, and they were metalized with aluminum. The faux T cells were imaged with scanning electron microscopy, confirming that they form a regular and complete array (FIG. 5b) in a variety of coverages. Next, a 561 nm laser light was introduced into the waveguides using a green laser pointer and a benchtop optical setup that included a 10× objective to focus light into the waveguide, a 20× objective to focus light out of the waveguide, and a silicon photodiode as the detector. The measured transmitted light power through the waveguide diminished by the presence of the metalized faux cells, proportional to the number of faux cells above (FIG. 6). The relationship was fit by a single exponential: power ($\mu W$)=$0.0159 \times exp(-0.202$ coverage %).

According to one embodiment, the preparation of the channels includes:
1) Introduce neat 3-cyanopropyl dimethyl chlorosilane into channel, room temp×30 min, wash out with acetonitrile, then water.
2) Introduce antibodies at 10 μg/mL (anti-CD3ε to capture T cells, anti-CD19 to capture B cells) and recombinant adhesion molecules ICAM-1-Fc and LFA-3-Fc (R&D Systems) at 10 μg/mL, room temp, for 30 min.
3) Wash out channels with phosphate buffered saline (PBS). Store at 4° C. Channels are now ready for use.
4) Measure waveguide throughput—this is the baseline value.

According to another embodiment, the capturing of the immune cells includes:
1) Introduce ~10 μL of whole blood, allow to settle/incubate for 2 minutes, then wash out with PBS.

In a further embodiment of the invention, the labeling of the cells includes:
1) Inject biotinylated antibodies to label cells specifically (e.g., pan-αβ-TCR for all T cells expressing αβ-TCRs, anti-CD4 for helper T cells, anti-CD20 for B cells) at 10 μg/mL, room temp×5 min. Wash out with PBS.
2) Inject streptavidin-gold 10 μg/mL, room temp×5 min. Wash out with PBS.
3) Inject Silver Enhancer solution (SPI Supplies), room temp×5 min. Wash out with water.

The waveguide throughput was measured, where output light represents the quantity of captured, labeled cells. Thus, large numbers of T cells are captured and specifically detected from whole blood.

Example experiments have been completed, where analysis was performed on mouse cells to demonstrate capturing immune cells in microfluidic channels. T cells and non-T cells were purified separately from mouse blood, spleen, and lymph nodes and injected into the channels. The presence of T cells captured in the channel was confirmed by fluorescence microscopy. Using these cells as positive and negative controls, T cells were detected specifically using a silver precipitation method, where the steps for capturing & detecting immune cells in microfluidic channels include preparation of the channels, capture of immune cells, labeling and detection. It should be noted that fluorescence microscopy is not used in the actual detection process, but was used to confirm the specific presence of T cells.

Figure 7:
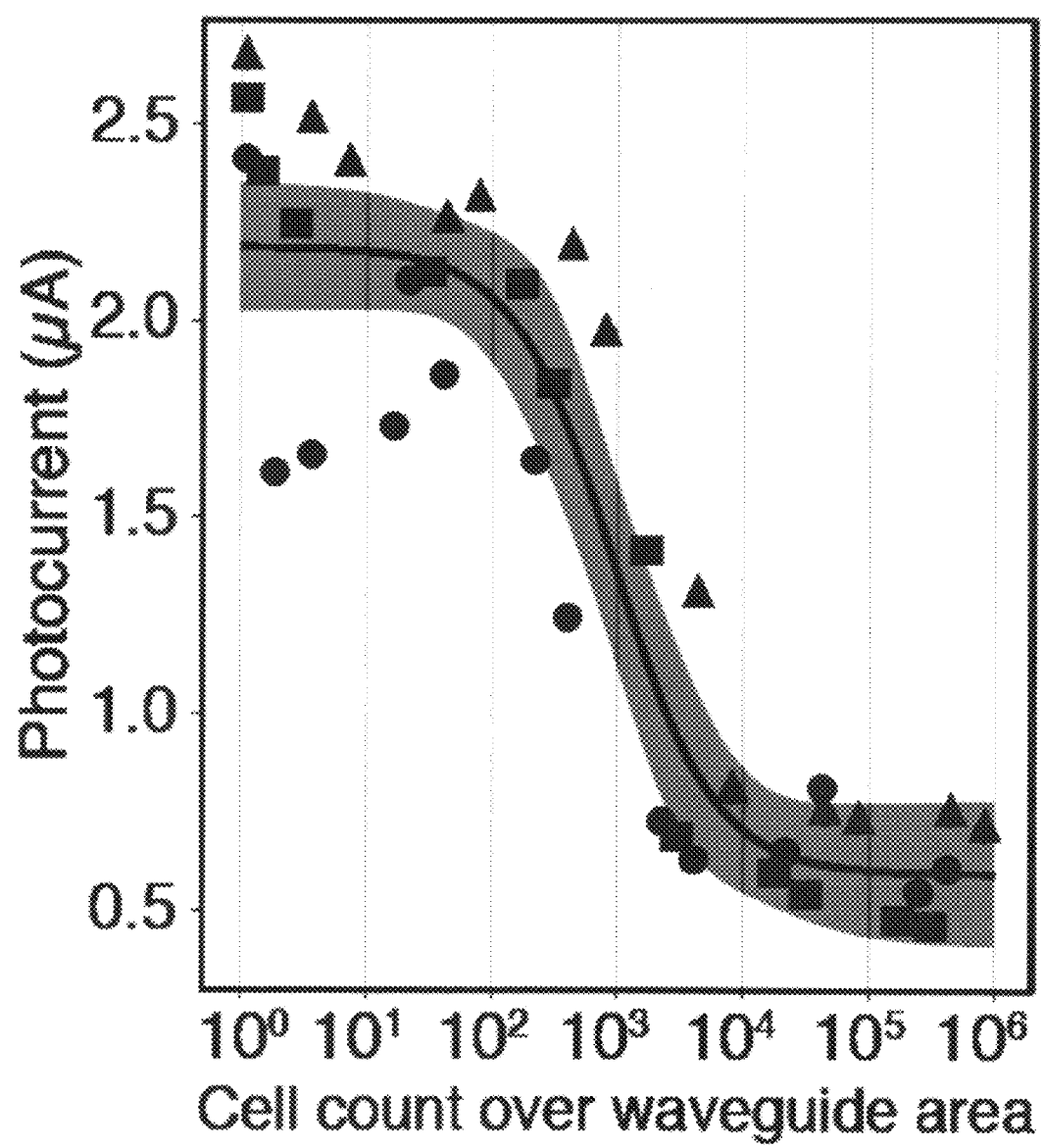
FIG. 7 shows a graph of experimental date from three experiments showing a decrease in signal upon serial addition of dilute cells, according to one embodiment of the invention.

Peripheral blood lymphocytes were counted (which express the cell-surface molecule CD45) from the whole blood. A PDMS microfluidic channel was positioned so that the lumen lay above the waveguide. To tag the cells for cell-type specific capture, goat anti-mouse IgG (Fc) ferromagnetic particles (Spherotech, USA) were coated with mouse biotin anti-human CD45 antibody (Biolegend, USA) (4° C. for 30 min with rocking). A magnet was glued beneath the waveguide glass to facilitate capture of the ferromagnetically-tagged cells within the channel. Peripheral blood mononuclear cells (PBMC) were isolated from venous blood of healthy adult donors after informed consent using density-gradient centrifugation (Ficoll-Paque, GE Healthcare, USA), were incubated with the antibody-coated ferromagnetic particles (4° C. for 30 min), then were counted by hemocytometer in duplicate. Following the incubation, the cells were washed in PBS and diluted serially to produce various concentrations. Suspensions containing increasing concentrations of bead-tagged PBMCs were added to the microfluidic channel over the waveguide chip, resulting in progressively higher numbers of bead-tagged cells covering the waveguide. Light microscopy and analysis with ImageJ was employed to count the number of cells that covered the waveguide area. Light through the blank waveguides elicited a photocurrent of 2.53±0.27 μA (95% CI, n=3 independent experiments). Cells were introduced gradually and allowed to settle on the waveguide surface for 10 minutes before a measurement of the transmitted light was taken by recording the photocurrent of the photodiode. It was found that increments of cells added reduced the photocurrent as shown in FIG. 7, where a decrease in signal is shown upon serial addition of dilute cells. Three independent experiments are shown (square, triangle, circle) with a sigmoidal fit and the 95% confidence interval of the fit. A saturating number of cells introduced into the channel (~1 million) reduced the photocurrent to 0.59±0.18 μA. Further, it was found that a 50% reduction in photocurrent was seen around the point at which ~950 lymphocytes had been added to the channel. These results show that the waveguide-based sensor could detect a very small number of cells from blood and could reasonably count the expected numbers of most cell types in the blood. Notably, low numbers of tagged cells generate more photocurrent, which makes this methodology ideal for screening for numerical deficiencies of cells, e.g., screening T cell counts in newborns to diagnose Severe Combined Immune Deficiency (SCID).

The example demonstrates enumeration of primary cells from whole blood by attenuation of waveguide-transmitted light. The invention works in ambient light, by avoiding the use of fluorescently-tagged reagents, which may have a short half-live due to sensitivity to light. Waveguides can be fabricated side by side, which enable multiplexing.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example multiple waveguides could sequentially underlie a microfluidic channel, which when functionalized to capture different cell types could allow a single device to count multiple cell types from the same drop of blood.

All such variations are considered to be within the scope and spirit of the present invention as defined by the following claims and their legal equivalents.

What is claimed:
1. A microfluidic detection device, comprising:
a) a planar waveguide;
b) a microfluidic channel disposed on said planar waveguide;

c) a light source which directs light through said planar waveguide;
d) a labeled cell disposed in said microfluidic channel, wherein said labeled cell lies in an evanescent field extending from said planar waveguide; and
e) a light detector disposed to receive light from said light source through said planar waveguide, wherein said evanescent field interacts with said labeled cell, wherein said light through said planar waveguide is altered according to a presence of said labeled cell in said microfluidic channel, wherein said labeled cell comprises a label selected from the group consisting of gold, iron, silver, tin, lead, magnesium, aluminum, selenium, platinum, mercury, erbium, terbium, nickel, cadmium, uranium, and composites salts or alloys thereof.

2. The microfluidic detection device of claim 1, wherein said planar waveguide comprises an ion-exchange planar waveguide.

3. The microfluidic detection device of claim 1, wherein said planar waveguide comprises a first layer disposed between a pair of second layers, wherein said first layer comprises a first refractive index and said second layers comprise a second refractive index, wherein said first refractive index is higher than said second refractive index, wherein light can be transported through said first layer.

4. The microfluidic detection device of claim 3, wherein said first layer comprises glass or polymer, wherein said second layers comprise photoresist or polymer of lower refractive index than said first layer.

5. The microfluidic detection device of claim 1, wherein said microfluidic channel comprises:
a) a sample input;
b) a sample output;
c) a reagent input;
d) a detection zone; and
e) a reagent output.

6. The microfluidic detection device of claim 2, wherein said ion-exchange waveguide is made from material selected from the group consisting of potassium and silver salts.

7. The microfluidic detection device of claim 1, wherein said light source is selected from the group consisting of laser, light emitting diode, and incandescent light bulb.

* * * * *